US00PP18460P2

(12) United States Plant Patent
van Delft

(10) Patent No.: US PP18,460 P2
(45) Date of Patent: Jan. 29, 2008

(54) ***COREOPSIS* PLANT NAMED 'LITTLE SUNDIAL'**

(50) Latin Name: *Coreopsis hybrida*
Varietal Denomination: Little Sundial

(75) Inventor: Luit van Delft, VP Noordwijkerhout (NL)

(73) Assignee: Future Plants Licentie B.V., Lissenbroek (NL)

( * ) Notice: Subject to any disclaimer, the term of this patent is extended or adjusted under 35 U.S.C. 154(b) by 0 days.

(21) Appl. No.: 11/509,515

(22) Filed: Aug. 24, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—S. B. McCormick-Ewoldt
(74) *Attorney, Agent, or Firm*—C. A Whealy

(57) ABSTRACT

A new and distinct cultivar of *Coreopsis* plant named 'Little Sundial', characterized by its compact and upright plant habit; low to moderately vigorous growth habit; freely basal branching habit; freely flowering habit; rotate single inflorescences with golden yellow and dark orange-colored ray florets; and moderately strong peduncles that hold the inflorescences above the foliar plane.

2 Drawing Sheets

Botanical designation: *Coreopsis hybrida.*
Cultivar denomination: 'Little Sundial'.

BACKGROUND OF THE INVENTION

The present invention relates to a new and distinct cultivar of *Coreopsis* plant, botanically known as *Coreopsis hybrida,* and hereinafter referred to by the name 'Little Sundial'.

The new *Coreopsis* originated from an open-pollination of an unnamed selection of *Coreopsis hybrida,* not patented, as the female, or seed, parent with an unknown selection of *Coreopsis hybrida,* as the male, or pollen, parent. The new *Coreopsis* was discovered and selected by the Inventor as a single flowering plant from within the progeny of the stated open-pollination grown in a controlled environment in Noordwijkerhout, The Netherlands in 2001.

Asexual reproduction of the new *Coreopsis* by cuttings in a controlled environment in Noordwijkerhout, The Netherlands since 2003, has shown that the unique features of this new *Coreopsis* are stable and reproduced true to type in successive generations.

SUMMARY OF THE INVENTION

The cultivar Little Sundial has not been observed under all possible environmental conditions. The phenotype may vary somewhat with variations in environment such as temperature and light intensity, without, however, any variance in genotype.

The following traits have been repeatedly observed and are determined to be the unique characteristics of 'Little Sundial'. These characteristics in combination distinguish 'Little Sundial' as a new and distinct cultivar of *Coreopsis:*

1. Compact and upright plant habit.
2. Low to moderately vigorous growth habit.
3. Freely basal branching habit.
4. Freely flowering habit.

5. Rotate single inflorescences with golden yellow and dark orange-colored ray florets.
6. Moderately strong peduncles that hold the inflorescences above the foliar plane.

Compared to plants of the female parent selection, plants of the new *Coreopsis* are more compact and are more freely flowering.

Plants of the new *Coreopsis* can be compared to plants of the *Coreopsis* cultivar Sterntaler, not patented. In side-by-side comparisons conducted in Lisserbroek, The Netherlands, plants of the new *Coreopsis* differed from plants of the cultivar Sterntaler in the following characteristics:

1. Plants of the new *Coreopsis* were more compact and more uniform than plants of the cultivar Sterntaler.
2. Plants of the new *Coreopsis* were more freely flowering than plants of the cultivar Sterntaler.

BRIEF DESCRIPTION OF THE PHOTOGRAPHS

The accompanying photographs illustrate the overall appearance of the new *Coreopsis.* The photographs show the colors as true as it is reasonably possible to obtain in colored reproductions of this type. Colors in the photographs may differ slightly from the color values cited in the detailed botanical description which accurately describe the colors of the new *Coreopsis.*

The photograph at the top of the first sheet comprises a side perspective view of a typical flowering plant of 'Little Sundial' grown in a container.

The photograph at the bottom of the first sheet is a close-up view of a typical leaf of 'Little Sundial'.

The photograph on the second sheet is a close-up view of a typical inflorescence of 'Little Sundial'.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown in Lisserbroek, The Netherlands during the summer and early autumn in an outdoor nursery and under conditions and practices which approximate those generally used in commercial *Coreopsis* production. During the production of the plants, day temperatures ranged from 14° C. to 32° C. and night temperatures ranged from 4° C. to 16° C. Measurements and numerical values represent averages for typical flowering plants. Plants were about one year old when the photographs and description were taken.

Botanical classification: *Coreopsis hybrida* cultivar Little Sundial.

Parentage:

*Female parent.*—Unnamed selection of *Coreopsis hybrida,* not patented.

*Male parent.*—Unknown selection of *Coreopsis hybrida,* not patented.

Propagation:

*Type.*—By cuttings.

*Time to develop roots.*—About 20 to 30 days at 18° C.

*Time to produce a rooted young plant.*—About 100 days at 22° C.

*Root description.*—Fine; light grey to white in color.

*Rooting habit.*—Freely branching; moderately dense.

Plant description:

*Plant form/growth habit.*—Compact, upright and uniform plant habit; inverted triangle; freely basal branching with dense foliage and inflorescences held above the foliage on moderately strong peduncles. Low to moderately vigorous growth habit.

*Plant height.*—About 18.5 cm.

*Plant diameter or spread.*—About 22 cm.

*Lateral branches.*—Length: About 2.3 cm. Diameter: About 2 mm. Internode length: About 1 cm. Aspect: Mostly upright to slightly outwardly spreading. Strength: Strong. Texture: Smooth, glabrous. Color: 143B.

Foliage description:

*Arrangement.*—Alternate, simple.

*Length.*—About 11.3 cm.

*Width.*—About 1.2 cm.

*Shape.*—Narrowly elliptic to narrowly oblanceolate; pinnatisect.

*Apex.*—Acute.

*Base.*—Narrowly attenuate.

*Margin.*—Entire.

*Texture, upper and lower surfaces.*—Smooth, glabrous; margins, pubescent.

*Venation pattern.*—Pinnate.

*Color.*—Developing foliage, upper surface: 143A. Developing foliage, lower surface: 138A. Fully expanded foliage, upper surface: 137A; venation, 144A. Fully expanded foliage, lower surface: 144A to 146B; venation, 144B to 144C.

*Petiole length.*—About 4.2 cm.

*Petiole diameter.*—About 2 mm.

*Petiole color, upper surface.*—144C.

*Petiole color, lower surface.*—145A.

Inflorescence description:

*Appearance.*—Rotate single inflorescence form with ray and disc florets. Inflorescences positioned above the foliage on moderately strong peduncles. Inflorescences face mostly upright. Freely flowering habit; about four inflorescences developing per lateral branch. Inflorescences persistent.

*Fragrance.*—Slightly fragrant.

*Time to flower.*—Under natural season conditions, plants flower from early September to mid-October in The Netherlands.

*Post-production longevity.*—Inflorescences maintain good substance for about three weeks on the plant.

*Inflorescence bud.*—Height: About 7 mm. Diameter: About 7 mm. Shape: Globular. Color: N199A to N200A tinged with close to 147A.

*Inflorescence size.*—Diameter: About 4.5 cm. Depth (height): About 1.8 cm. Disc diameter: About 9 mm. Receptacle diameter: About 9 mm. Receptacle height: About 7 mm.

*Ray florets.*—Shape: Obovate. Length: About 2 cm. Width: About 1.4 cm. Apex: Praemorse. Base: Rounded. Texture, upper and lower surfaces: Smooth, glabrous. Number of ray florets per inflorescence: About 20 arranged in one whorl. Color: When opening, upper surface: 14A; towards the base, 172A. When opening, lower surface: 14B. Fully opened, upper surface: 17A; towards the base, 175B. Fully opened, lower surface: 14B.

*Disc florets.*—Shape: Tubular; apex dentate. Length: About 1.1 cm. Diameter, apex: About 2.5 mm. Diameter, base: About 1 mm. Number of disc florets per inflorescence: About 60. Color: Immature: 163A. Mature: Apex: 22A. Mid-section: 19A. Base: 19C to 19D.

*Phyllaries.*—Quantity per inflorescence: About ten. Length: About 9 mm. Width: About 4.5 mm. Shape: Ovate. Apex: Acute. Base: Cuneate. Margin: Entire. Texture, upper and lower surfaces: Smooth, glabrous. Color, upper and lower surfaces: 152C; towards the base, 146B.

*Peduncles.*—Length: About 11 cm. Diameter: About 1.5 mm. Strength: Moderately strong. Aspect: Mostly upright to about 20° from vertical. Texture: Smooth, glabrous. Color: 143A.

*Reproductive organs.*—Androecium: Quantity per disc floret: Two. Anther shape: Linear. Anther length: About 2 mm. Anther color: 165B. Filament color: 145D. Pollen amount: Scarce. Pollen color: 14B. Gynoecium: Pistil length: About 8 mm. Stigma shape: Cleft. Stigma color: 21A. Style length: About 6 mm. Style color: 1B to 1C. Ovary color: 145C.

*Seed/fruit.*—Seed and fruit production has not been observed.

Disease/pest resistance: Plants of the new *Coreopsis* have not been shown to be resistant to pathogens and pests common to *Coreopsis.*

Garden performance: Plants of the new Clematis have exhibited good tolerance to rain and wind and have been observed to be suitable for USDA Zones 6 to 10.

It is claimed:

1. A new and distinct *Coreopsis* plant named 'Little Sundial' as illustrated and described.

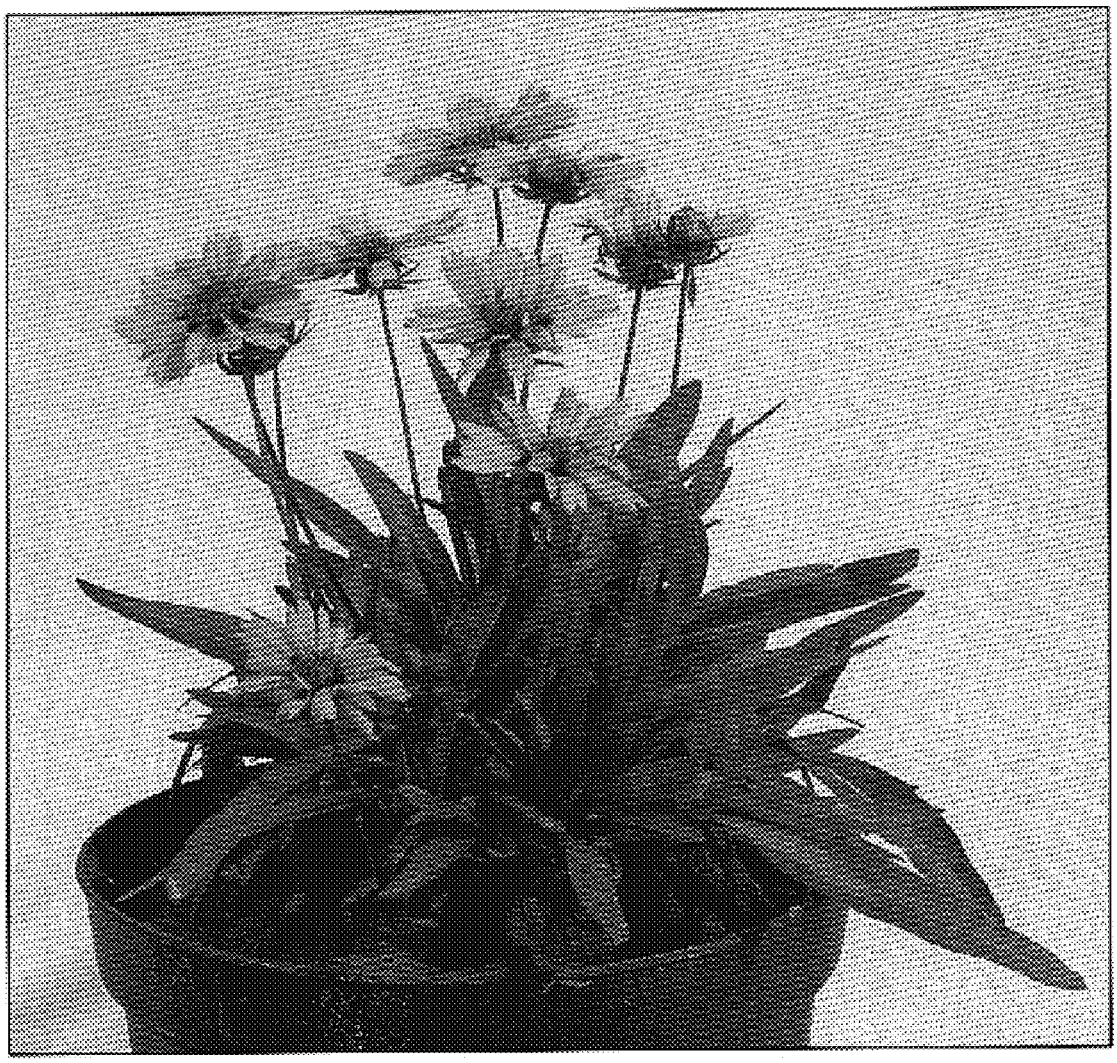
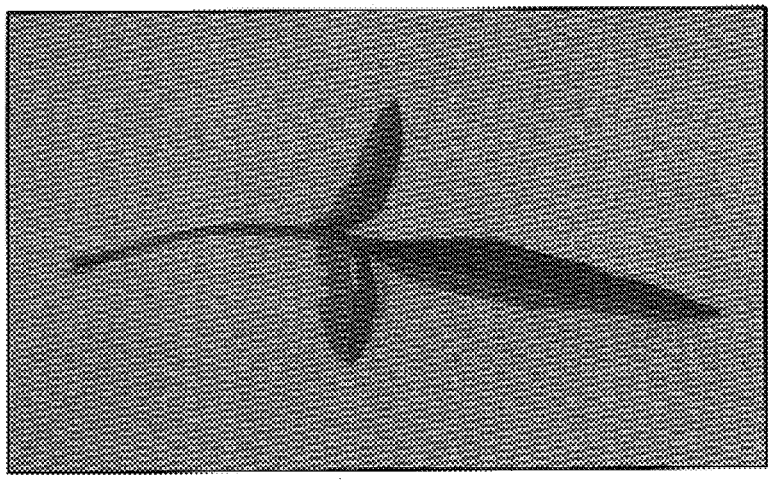

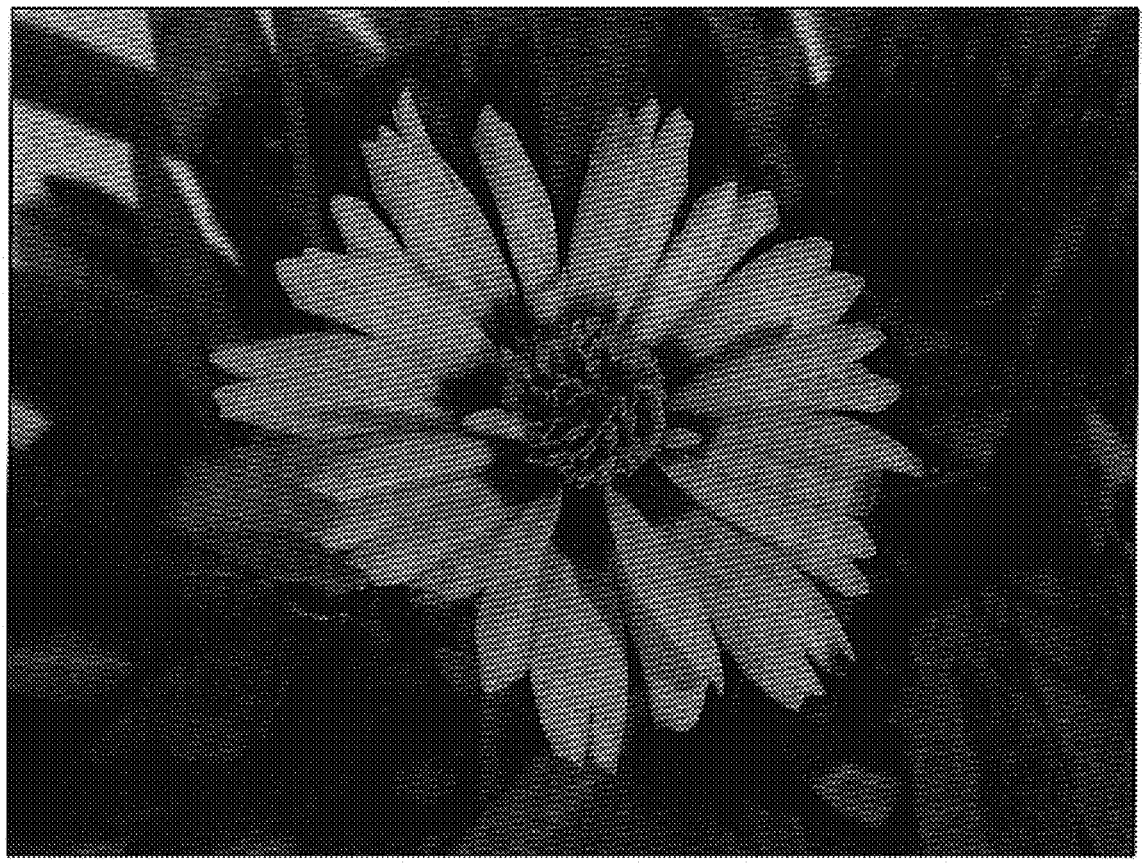

* * * * *